(12) United States Patent
Wand (10) Patent No.: US 9,572,611 B2
(45) Date of Patent: Feb. 21, 2017

(54) SURGICAL SCREW MAGAZINE (71) Applicant: Aesculap AG, Tuttlingen (DE)

(72) Inventor: Matthias Wand, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 307 days.

(21) Appl. No.: 14/208,197

(22) Filed: Mar. 13, 2014

(65) Prior Publication Data

US 2014/0309702 A1   Oct. 16, 2014

(30) Foreign Application Priority Data

Apr. 15, 2013 (DE) .......................... 10 2013 103 780
Mar. 5, 2014 (DE) .......................... 10 2014 102 907

(51) Int. Cl.
*A61B 17/86* (2006.01)
*A61B 17/17* (2006.01)
*A61B 17/80* (2006.01)

(52) U.S. Cl.
CPC .......... *A61B 17/865* (2013.01); *A61B 17/1728* (2013.01); *A61B 50/20* (2016.02); *A61B 50/22* (2016.02); *A61B 50/30* (2016.02); *A61B 17/80* (2013.01); *A61B 17/86* (2013.01)

(58) Field of Classification Search
CPC ............................ A61B 17/865; A61B 17/808
See application file for complete search history.

(56) References Cited

U.S. PATENT DOCUMENTS

| 3,812,961 | A | 5/1974 | Merrick et al. |
| 4,299,221 | A | 11/1981 | Phillips et al. |
| 5,129,292 | A | 7/1992 | Albert |
| 6,128,982 | A | 10/2000 | Gwin, Sr. |
| 6,328,746 | B1 | 12/2001 | Gambale |
| 6,620,011 | B2 | 9/2003 | Obermeier et al. |
| 7,588,576 | B2 * | 9/2009 | Teague ............... A61B 17/1735 606/280 |
| 8,414,594 | B2 | 4/2013 | Berger et al. |
| 9,271,732 | B2 * | 3/2016 | Walker .................. A61B 17/10 |
| 2003/0118424 | A1 | 6/2003 | Obermeier et al. |
| 2004/0204717 | A1 | 10/2004 | Fanger et al. |
| 2005/0177163 | A1 | 8/2005 | Abdou |
| 2005/0261691 | A1 | 11/2005 | Hester et al. |
| 2005/0283155 | A1 | 12/2005 | Jacene et al. |
| 2006/0149250 | A1 | 7/2006 | Castaneda et al. |
| 2006/0229618 | A1 | 10/2006 | Dube |

(Continued)

FOREIGN PATENT DOCUMENTS

| DE | 296 19 321 | 3/1997 |
| DE | 299 13 390 | 10/1999 |

(Continued)

*Primary Examiner* — Andrew Yang
(74) *Attorney, Agent, or Firm* — Lipsitz & McAllister, LLC (57) ABSTRACT

In order to provide the surgeon with means which allow the surgeon to use screws in a gentle and time-efficient manner, particularly in the setting of craniotomy, a surgical screw magazine is proposed comprising a holding device and a plurality of surgical screws, the holding device of said surgical screw magazine comprising a screw-receiving body which comprises for each of the screws a receiving opening in which the screws are at least substantially received, wherein the receiving openings are formed in the screw-receiving body spaced apart a predetermined distance from one another.

17 Claims, 5 Drawing Sheets

(56) References Cited

U.S. PATENT DOCUMENTS

2007/0162013 A1 7/2007 Jacene et al.
2011/0004254 A1 1/2011 Beger et al.

FOREIGN PATENT DOCUMENTS

| DE | 101 62 635 | 7/2003 |
| DE | 10 2008 010 333 | 8/2009 |
| WO | WO 2007/070196 | 6/2007 |

* cited by examiner

SURGICAL SCREW MAGAZINE

This application claims the benefit of German application number 10 2013 103 780.1 filed on Apr. 15, 2013 and German application number 10 2014 102 907.0 filed on Mar. 5, 2014, which are incorporated herein by reference in their entirety and for all purposes.

BACKGROUND OF THE INVENTION

The invention relates to a novel surgical screw magazine comprising a holding device and a plurality of surgical screws.

Screw magazines comprising a holding device and a plurality of screws arranged thereon are known per se in the general art of fastening and are disclosed for example in DE 101 62 635 A1.

However, these screw magazines are not suited for use in the field of surgery because of the risk of injury to bones and tissue in the vicinity of the site of application, making their use in the field of surgery prohibitive.

It is an object of the present invention to provide a means which allows the surgeon to use screws in a gentle and time-efficient manner, particularly in the setting of craniotomy.

SUMMARY OF THE INVENTION

This object is achieved by the novel surgical screw magazine having the features of claim 1.

The surgical screw magazines constructed in accordance with the invention are particularly suited for craniotomy procedures in which a patient's skull cap is to be re-closed using a previously prepared skull fragment. In this regard, frequently used systems are those comprising what are known as bone plates, made of metal or plastics materials, as are described for example in DE 299 13 390 U1.

The bone plates establish a connection between two bone parts, wherein the bone plates are joined to the bone parts of the skull cap by surgical screws. The screwing-in of these surgical bone screws very often places high manual demands on the surgeon. He or she must not only fixate the plates against slipping out of place but must also at the same time take a screw from a magazine, start it securely and, frequently by exertion of quite an amount of force, drive it into the bone part without angular misalignment. During an operation the patient's skull is rigidly fixated, and in many cases this makes the process of driving the screws even more difficult because the surgeon must for example screw sideways at an ergonomically awkward angle.

The screw magazine constructed in accordance with the invention now provides a plurality of surgical screws, particularly for use as bone screws in craniotomy, said screws being both easy and safe to handle so that there is no danger to the tissue and bones in the immediate vicinity of the site of application. Moreover, the receiving openings for the screws can at the same time form a guide for the screws so that angular misalignment of the screws during the application thereof is prevented.

Furthermore, the surgical screw magazine constructed in accordance with the invention prevents the screws from being lost, as the screws are substantially fully received by the screw-receiving body and the receiving openings thereof. The surgeon's task is thereby considerably simplified because the need for separating and picking up the screws with the screwdriver is obviated.

Optionally, the surgical screw magazine constructed in accordance with the invention can be adapted for feed with a corresponding screwing machine which automatically positions the screws stored in a screw-receiving body.

Preferably, in the surgical screw magazine constructed in accordance with the invention, the screw-receiving body is fabricated from an elastic material, for example a silicone material, which when the screw is being screwed in can yield and can recede in a radial direction of the screw and therefore does not hinder the screw-driving process. Nonetheless, the screws can still be guided by way of the receiving opening during the screwing-in process.

The screw-receiving body can be pulled off the screw after same is fully driven in, typically with its screw head countersunk, unless such separation occurs substantially automatically.

Finally, it is also conceivable for the receiving openings each to comprise a point of weakness by which the screw can be separated from the surrounding screw-receiving body at a point in time at which the screw is already held securely in the bone material and the screwing-in process may be completed separately from the screw-receiving body.

The previously mentioned elastic materials are preferably light-transmissive, i.e., transparent or at least translucent, so that the screw-receiving body can be seen through to view at least the contours of the application site and optionally the body of the bone plate that is to be fastened by the screws.

Preferably, the receiving openings of the screw-receiving bodies of the surgical screw magazines constructed in accordance with the invention are configured as through-openings. Alternatively, the receiving openings can also be configured as blind holes, with the tip of the respective screw being arranged at the closed end of the receiving opening, thereby ensuring that the tip of the screw cannot come into contact with the surrounding tissue or the bone before the surgeon intentionally starts the screwing process.

As mentioned previously, the receiving openings are preferably configured as guides for the screws, i.e., in addition to holding the screws in a predetermined position while in the rest position, the mechanical properties of the screw-receiving body are selected such that, in spite of the elasticity of the screw-receiving body, unintentional angular misalignment of the screws during the application thereof is prevented.

It is preferred for the screws to be held in the receiving openings of the screw-receiving body by way of a form-locking engagement and/or a force-locking engagement.

In accordance with another alternative embodiment of the surgical screw magazines constructed in accordance with the invention, provision may be made for the screws to be arranged in the screw-receiving body such that the screws are held in the receiving openings with their tips projecting slightly from the screw-receiving body. This facilitates alignment of the surgical screw magazine with bone plates that are to be placed on and attached to the bone material and with the through-openings thereof.

In accordance with a further variant, provision may be made for the screws to be arranged in the receiving openings with their screw head protruding at least partially from the screw-receiving body. This facilitates engagement of the screw driver with the screw, in particular where the screws are small.

Typically, the screws are arranged in the screw-receiving body in substantially parallel alignment with one another and can thus be applied one by one without interfering with one another.

One form of the surgical screw magazines includes configuring the screw-receiving body as a screw belt in which the receiving openings for the screws are formed in the screw belt in successive relation to one another in a single row or in a plurality of parallel rows.

In accordance with an alternative scheme of the screw magazine constructed in accordance with the invention, the screw-receiving body is configured as a volumetric body having three major directions of extension.

The outer contour of the volumetric body, when viewed in plan view of the receiving openings of the screw-receiving body, may be configured in a rectangular shape, a polygonal shape, a round shape or also in an oval shape.

It is preferred for the screw receiving-body to be configured in the shape of a block, for example in the shape of a cuboid or polygon, the receiving openings for the screws being configured in the screw-receiving body in a predetermined application pattern. Said application pattern may for example correspond to the through-opening pattern of a bone plate for which the screws are held ready in the screw magazine.

In accordance with a further variant of the surgical screw magazines, provision may be made for the screw magazine to comprise one or more bone plates arranged on the side of the screw-receiving body towards which the tips of the screws face.

Thus, for example, a screw magazine of the present invention that is configured in a screw belt-like manner may have a plurality of bone plates of substantially linear configuration arranged thereon one behind the other.

If the bone plates to be applied have a geometry that is more complex than the linear geometry, the screw-receiving body is preferably configured conforming to the geometry of the bone plate.

More preferably, in such a case the bone plate is releasably connected to the holding device of the screw magazine, in particular to the screw-receiving body, so that the alignment of the screws with a given screw application pattern (for example the through-openings) of the bone plate is predetermined from the outset, i.e., before the surgeon starts applying the bone plate. This manner of applying the bone plate brings still further simplification to the surgeon and thus also makes using the bone plate safer for the patient.

The releasable connection of the holding device, or screw-receiving body, to the bone plate may be a substance-to-substance bond, a form-locking engagement and/or a force-locking engagement, for example by way of a releasable adhesive bond or by snapping together the bone plate and the elastically yielding material of the screw-receiving body.

These and further advantages of the invention are described in more detail below with reference to the drawings.

DETAILED DESCRIPTION OF THE INVENTION

Figure 1:
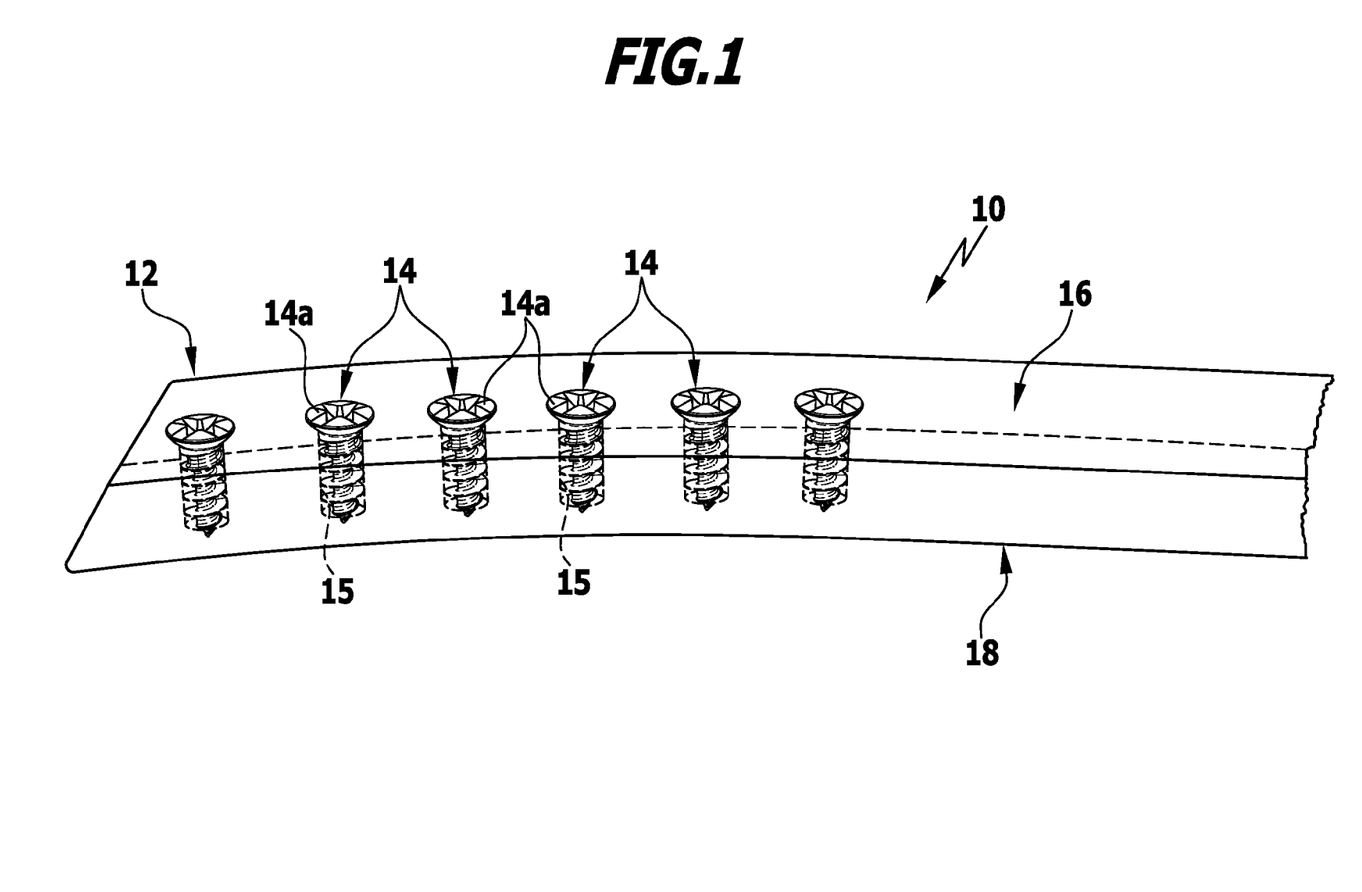
FIG. 1 is a first embodiment of a surgical screw magazine constructed in accordance with the invention.

Shown in FIG. 1 is a surgical screw magazine 10 constructed in accordance with the invention, comprising a holding device which is configured as a screw belt 12 and in the present case is to be equated with the screw-receiving body of the surgical screw magazine 10.

Held in the screw belt 12, in receiving openings 15 thereof, are a multiplicity of screws 14 arranged in linear relationship one behind the other in a single row.

In the present exemplary embodiment, the receiving openings 15 are configured as through-openings which extend from the upper side 16 of the screw belt 12 to the underside 18 thereof.

In the surgical screw magazine 10 constructed in accordance with the invention, the thickness of the holding device, or screw-receiving body 12, and hence the distance between the upper side 16 and the underside 18 is selected such that the screws 14 are essentially fully received in the receiving openings 15, with only the screw head 14a of the screws 14 projecting slightly from the surface 16 of the screw belt 12.

In particular, with this embodiment of the surgical screw magazine 10, the arrangement of the screws 14 in the receiving openings 15 is selected such that the tips of the screws 14 do not protrude beyond the underside 18 of the screw belt 12. Optionally, the receiving openings 15 may be configured as a blind hole, with the tips of the screws 14 then being placed at the closed end of the receiving openings 15.

This precludes injury to bones or tissue of a patient being treated in handling the screw magazine constructed in accordance with the invention.

The material used to form the screw belt 12 is preferably a transparent or at least translucent silicone material so that the surgeon is able to view during the process of applying the screws 14 whether the particular screw 14 to be applied is properly located over the bone plate that is to be fixated and over the screw position thereof, which may for example be a through-opening provided therefor.

The receiving openings 15 can receive the screws 14 in a close fit relationship therewith, thereby affording guidance to the screws 14 as these are screwed into place. In particular, this is possible without the need for further measures because the elastic silicone material of the screw belt 12 can yield laterally to the screws 14 as they are screwed into place and thus creates room for the passage of the screw heads 14a. Owing to the elasticity of the silicone material, once the screw 14 is fully screwed into place, the screw belt can be separated from that fully applied screw with little physical effort and without fragments of the screw belt being torn off. The separation between the screw 14 and the screw belt 12 can be facilitated further by the receiving opening having its end adjacent the underside 18 slightly enlarged.

Figure 2:
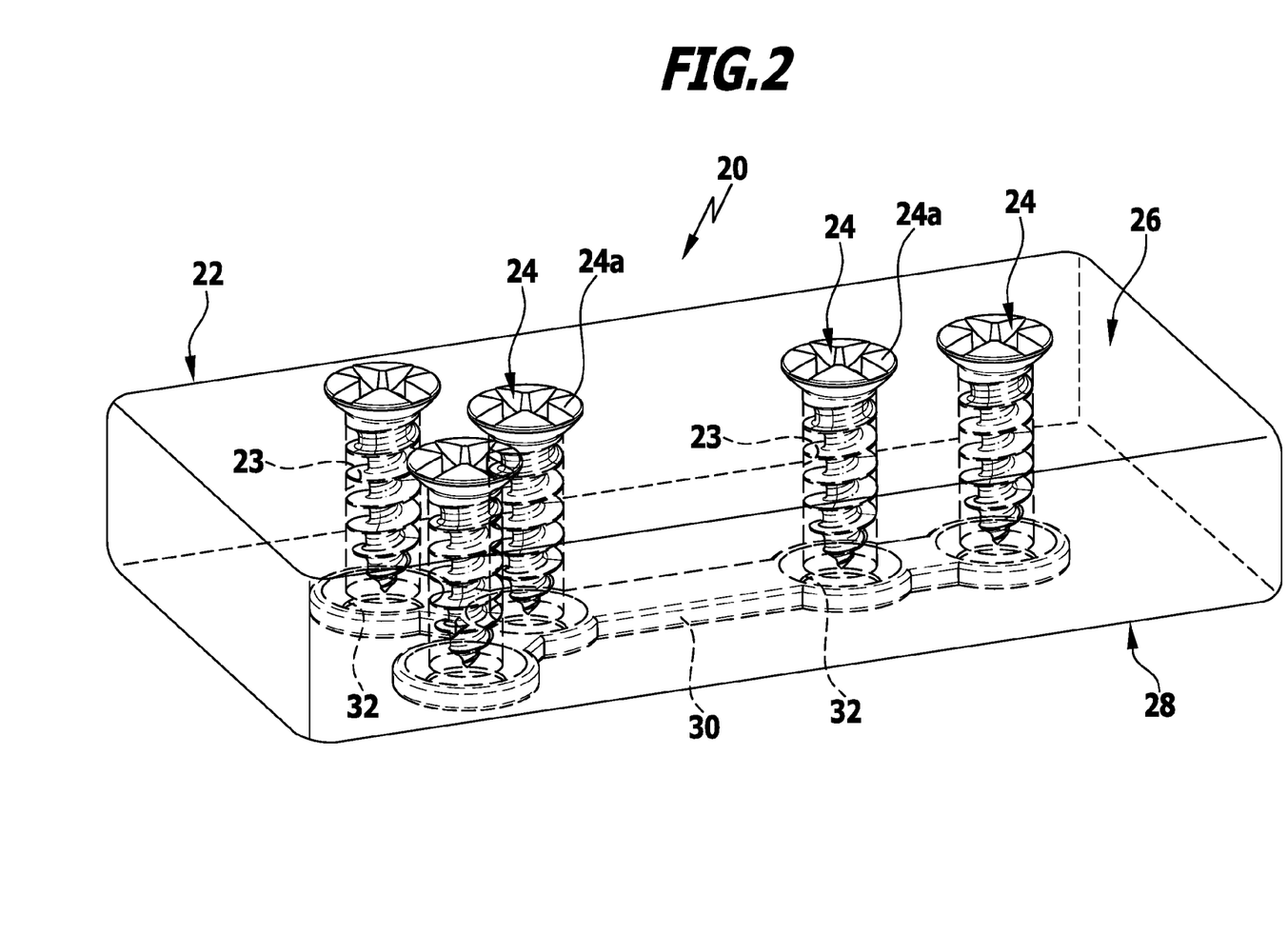
FIG. 2 is a second embodiment of a surgical screw magazine constructed in accordance with the invention, shown as having a bone plate held thereon.

FIG. 2 illustrates another embodiment of a surgical screw magazine 20 constructed in accordance with the invention, comprising a holding device 22 having a cuboid-shaped basic structure.

The holding device 22, which again is to be equated with the screw-receiving body, has arranged therein four receiving openings 23 which receive screws 24 in an arrangement corresponding to the arrangement of through-openings 32 in a bone plate 30.

Typically, the screw heads 24a of the screws 24 protrude slightly beyond the upper side 26 of the screw-receiving body 22.

The bone plate 30 is arranged at the underside 28 of the screw-receiving body 22 and is fixed to said underside 28 for example by a releasable adhesive bond.

Alternatively, provision may be made for the holding device 22 to hold the bone plate 30 in a releasable form-locking and/or force-locking engagement in the predetermined position thereof in which the through-openings 32 of the bone plate 30 are aligned with the receiving openings 23 in the screw-receiving body 22.

Since the bone plate 30 is held beneath the screw-receiving body and surrounds the tips of the screws 24 with the through-openings 32 thereof, with this embodiment the screws 24 may be arranged in the screw-receiving body 22 such that the tips of the screws 24 protrude slightly beyond the underside 28 of the screw-receiving body 22.

Figure 3:
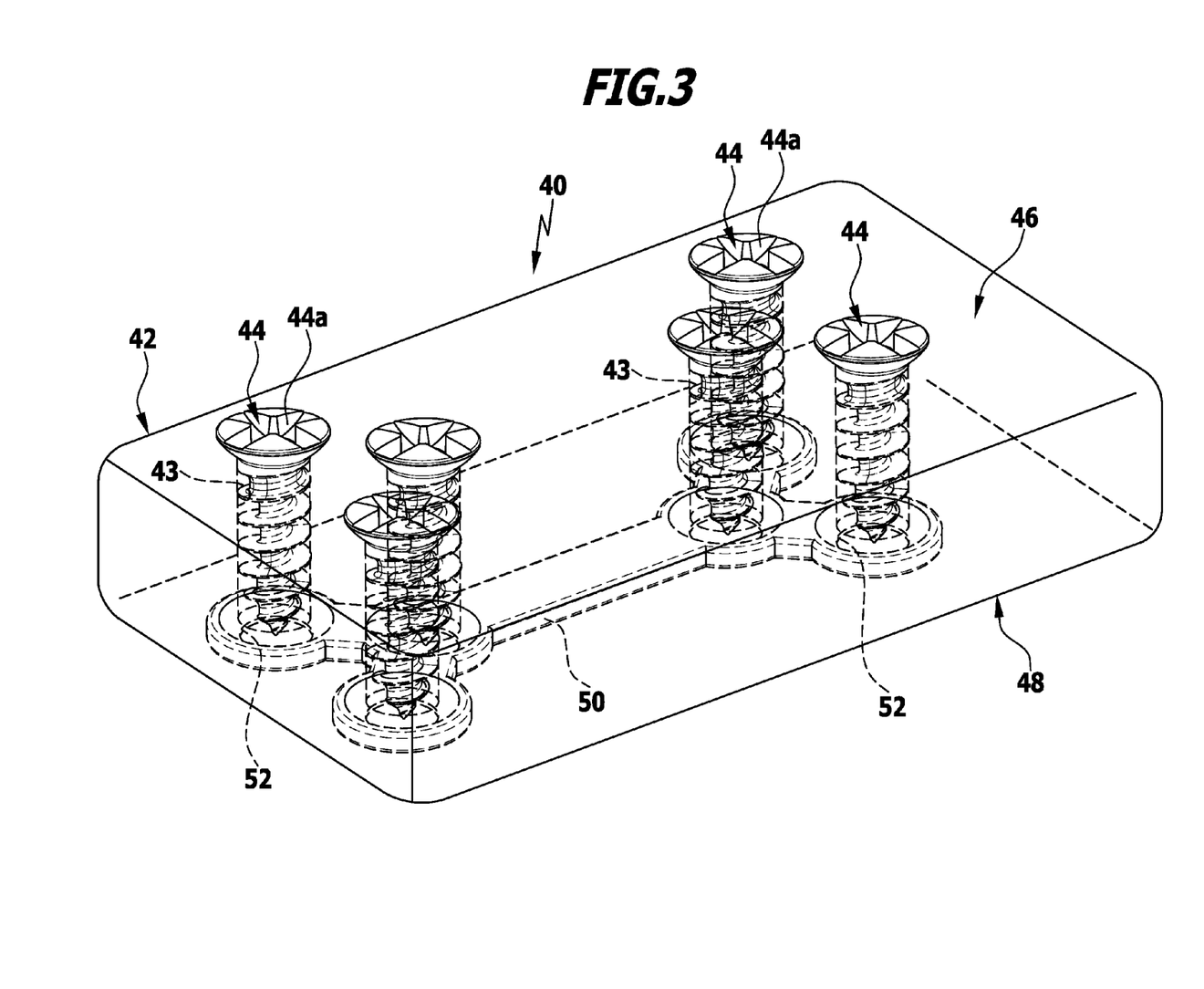
FIGS. 3 to 5 illustrate further variants of the second embodiment of the surgical screw magazine constructed in accordance with the invention.

FIG. 3 shows another embodiment of a surgical screw magazine 40 constructed in accordance with the invention, likewise comprising a cuboid-shaped basic body of a screw-receiving body 42 which in the present case serves as a holding device of the surgical screw magazine 40.

Arranged within the screw-receiving body 42 are receiving openings 43 which receive six screws 44 in an arrangement that corresponds to the geometry of a bone plate 50.

The screw heads 44a of the screws 44 protrude slightly from the upper side 46 of the screw-receiving body 42, while the tips of the screws 44 project only slightly from the underside 48 of the screw-receiving body 42.

Again, the underside 48 of the screw-receiving body 42 has the above-mentioned bone plate 50 with its screw through-openings 52 arranged such that the latter are in alignment with the receiving openings 43 for the screws 44.

Again, the bone plate 50 and the screw-receiving body 42 may be releasably connected to each other, such as by an adhesive bond or a force-locking and/or form-locking engagement.

Figure 4:
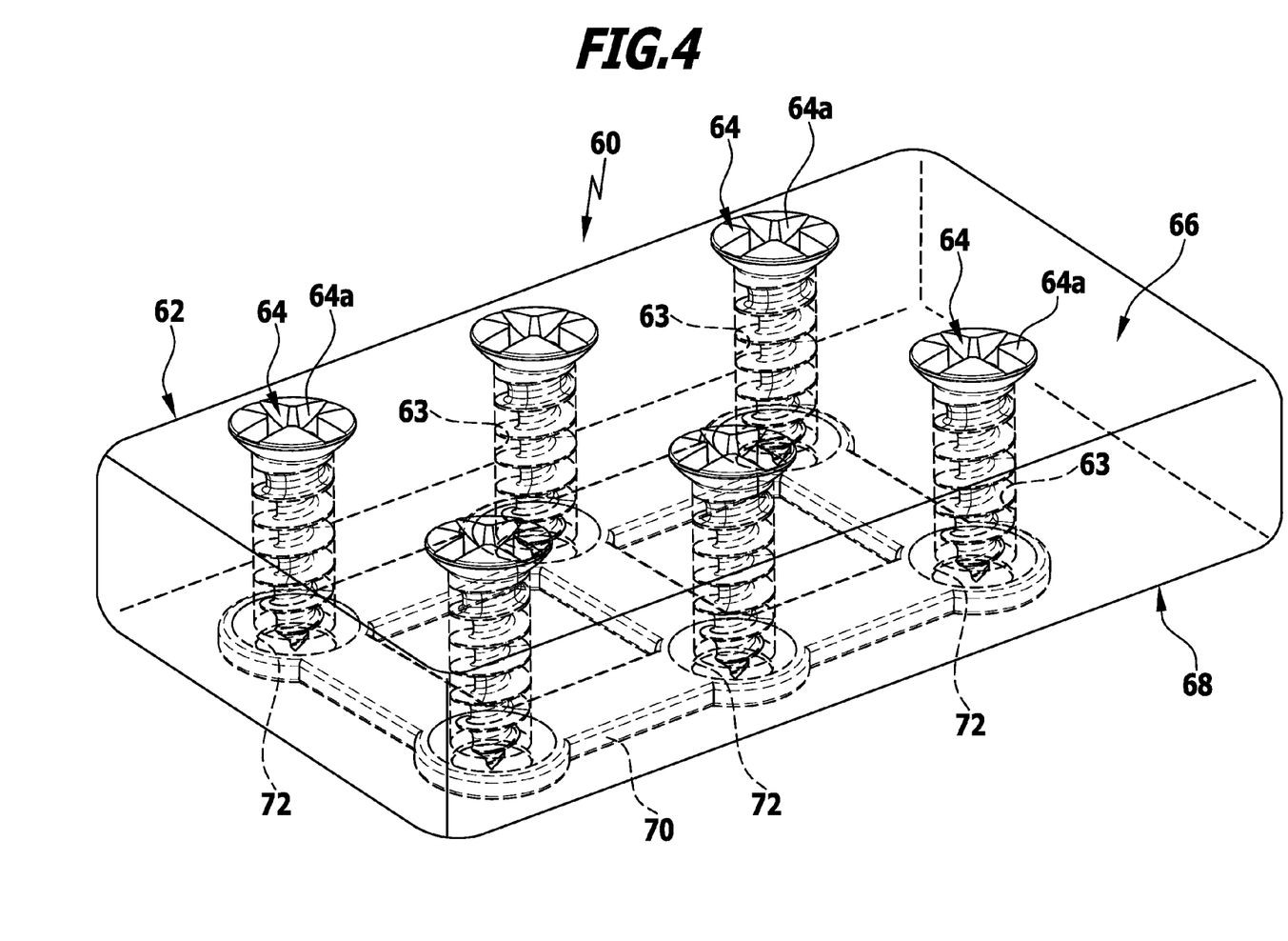

A further alternative embodiment of a surgical screw magazine 60 is depicted in FIG. 4, in which a screw-receiving body 62 comprises receiving openings 63 for screws 64 which are arranged in the screw-receiving body 62 in an arrangement corresponding to the arrangement of through-openings 72 of a bone plate 70. Again, the bone plate 70 is releasably held at the underside 68 of the screw-receiving body 62.

Figure 5:
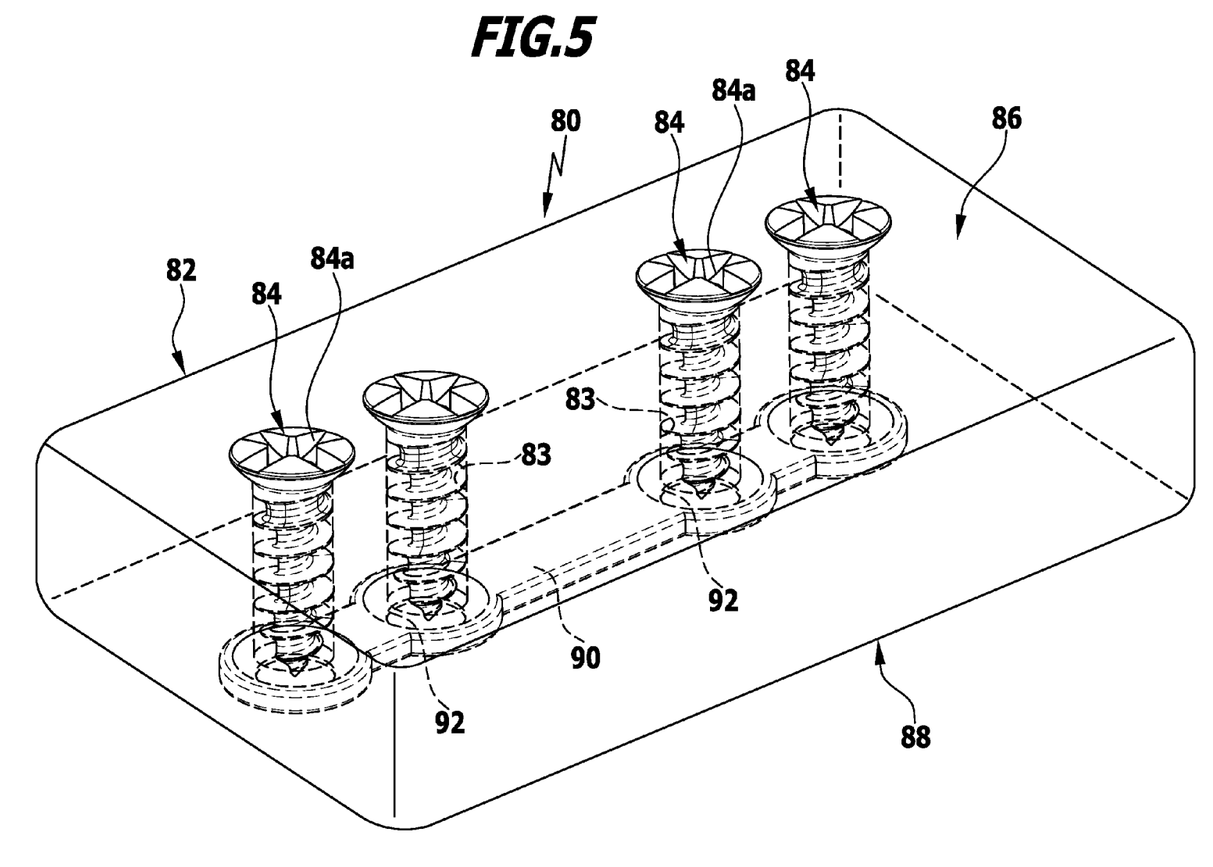

FIG. 5 shows a further embodiment of a surgical screw magazine 80 in which receiving openings 83 for receiving four screws 84 are formed in the screw-receiving body 82, said receiving openings 83 being arranged in linear relationship one behind the other in a row and spaced apart at different distances from one another.

Again, a bone plate 90 comprising through-openings 92 is releasably attached to the underside 88 of the screw-receiving body 82 such that the through-openings 92 are arranged in aligned relationship with the receiving openings 83 for the screws 84.

In the previously discussed embodiments of the surgical screw magazine of FIGS. 2 to 5, the screw-receiving bodies are shown to be cuboid-shaped. It is understood, however, that the screw-receiving bodies may have geometries different from that and may in particular have a geometry that is adapted to the geometry of the bone plate held on the screw-receiving body.

Moreover, it is within the scope of the present invention for a single screw-receiving body to have a plurality of bone plates arranged at the underside thereof and, therefore, for a screw-receiving body to comprise receiving openings for screws that are associated with a plurality of bone plates.

This arrangement may for example also be implemented in the screw belt of FIG. 1, for example in the context of using bone plates as are used for example for application in the exemplary embodiment of FIG. 5. The receiving openings in the screw belt are then no longer arranged one behind the other in a single row and spaced apart at equal distances as shown in FIG. 1 but spaced apart at varying distances as correspond for example to the distances of the through-openings 92 in the bone plate 90.

Moreover, it is of course also conceivable for a screw belt to comprise a plurality of parallel rows of screw-receiving openings so that bone plates as are used for example in FIGS. 2 to 4 can be releasably fixed one behind the other to the underside of the screw belt.

With each of the embodiments as discussed previously, the invention significantly facilitates the surgeon's task in applying the screws, since these are securely received and positioned in the screw-receiving body for their use. At the same time, the screws can be given guidance and orientation by way of the receiving openings, wherein the use of the elastic, transparent material additionally greatly facilitates for the surgeon application of the screws at the predetermined site.

The surgeon not only has the advantage of being able to handle the better graspable screw magazine in lieu of the individual bone screws, some of which are very small, but also, as shown in the example of FIGS. 2 to 5, has presented to him or her the bone plates in correct orientation with respect to the screws so that the surgeon can focus his or her entire attention on correctly aligning the bone plate on the patient.

The invention claimed is:

1. Surgical screw magazine comprising:
a holding device, and
a plurality of surgical screws,
the holding device comprising a screw-receiving body which comprises for each of the screws a receiving opening in which the screws are at least substantially received,
wherein:
the receiving openings are formed in the screw-receiving body spaced apart a predetermined distance from one another; and
the screw-receiving body is made entirely of an elastic silicone material which is light-transmissive.

2. Surgical screw magazine in accordance with claim 1, wherein the receiving openings are configured as through-openings.

3. Surgical screw magazine in accordance with claim 1, wherein the receiving openings are configured as guides for the screws.

4. Surgical screw magazine in accordance with claim 1, wherein the screws are held in the receiving openings by way of at least one of a form-locking engagement and a force-locking engagement.

5. Surgical screw magazine in accordance with claim 1, wherein the screws are arranged in the receiving openings with tips of the screws protruding beyond the screw-receiving body.

6. Surgical screw magazine in accordance with claim 1, wherein the screws are arranged in the receiving openings with screw heads of the screws protruding at least partially beyond the screw-receiving body.

7. Surgical screw magazine in accordance with claim 1, wherein the screws are arranged in the screw-receiving body in substantially parallel alignment with one another.

8. Surgical screw magazine in accordance with claim 1, wherein the screw-receiving body is configured as a screw belt, with the receiving openings for the screws being formed in the screw belt one behind the other in a single row.

9. Surgical screw magazine in accordance with claim 1, wherein the screw-receiving body is configured as a volumetric body having three major directions of extension.

10. Surgical screw magazine in accordance with claim 9, wherein an outer contour of the volumetric body, when viewed in plan view of the receiving openings of the screw-receiving body, is configured in one of a rectangular shape, a polygonal shape, a round shape or an oval shape.

11. Surgical screw magazine in accordance with claim 9, wherein:
- the screw-receiving body is configured in a shape of a block, and
- the receiving openings for the screws are formed in the screw-receiving body in a predetermined application pattern.

12. Surgical screw magazine in accordance with claim 11, wherein the application pattern corresponds to a selected bone plate.

13. Surgical screw magazine in accordance with claim 1, further comprising one or more bone plates on a side of the screw-receiving body towards which tips of the screws face.

14. Surgical screw magazine in accordance with claim 13, wherein the one or more bone plates are releasably connected to the holding device directly.

15. Surgical screw magazine in accordance with claim 14, wherein the one or more bone plates are releasably connected to the holding device by way of at least one of an adhesive bond, a form-locking engagement, and a force-locking engagement.

16. Surgical screw magazine in accordance with claim 13, wherein the one or more bone plates are releasably connected to the screw-receiving body directly.

17. Surgical screw magazine comprising:
- a holding device, and
- a plurality of surgical screws,
- the holding device comprising a screw-receiving body which comprises for each of the screws a receiving opening, a corresponding one of the screws being at least substantially received in each of the receiving openings, wherein:
- the receiving openings are formed in the screw-receiving body spaced apart a predetermined distance from one another;
- the screw-receiving body is made entirely of an elastic material which is light-transmissive; and
- each of the receiving openings comprises a point of weakness by which the corresponding screw can be separated from the surrounding screw-receiving body.

* * * * *